(12) United States Patent
Alzaga et al.

(10) Patent No.: US 11,490,984 B2
(45) Date of Patent: Nov. 8, 2022

(54) ALIGNING ELEMENT FOR GUIDING A NEEDLE, ALIGNING ARRANGEMENT, GUIDE ARRANGEMENT, TREATMENT ARRANGEMENT AND METHOD

(71) Applicant: Siemens Healthcare GmbH, Erlangen (DE)

(72) Inventors: Amilcar Alzaga, Nuremberg (DE); Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 624 days.

(21) Appl. No.: 16/547,129

(22) Filed: Aug. 21, 2019

(65) Prior Publication Data
US 2020/0085527 A1    Mar. 19, 2020

(30) Foreign Application Priority Data
Sep. 13, 2018    (DE) ...................... 10 2018 215 599.2

(51) Int. Cl.
*A61B 90/13*    (2016.01)
*A61B 17/34*    (2006.01)
*A61B 34/20*    (2016.01)

(52) U.S. Cl.
CPC .......... *A61B 90/13* (2016.02); *A61B 17/3403* (2013.01); *A61B 34/20* (2016.02); *A61B 2017/3405* (2013.01); *A61B 2034/2055* (2016.02)

(58) Field of Classification Search
CPC ..... A61B 90/13; A61B 17/3403; A61B 34/20; A61B 2017/3405; A61B 2034/2055
See application file for complete search history.

(56) References Cited

U.S. PATENT DOCUMENTS

| 5,437,280 A | 8/1995 | Hussman |
| 5,810,841 A | 9/1998 | Mcneirney |
| 9,095,361 B2 | 8/2015 | Baldwin |
| 2001/0053915 A1 | 12/2001 | Grossman |

(Continued)

FOREIGN PATENT DOCUMENTS

| DE | 102010031943 A1 | 1/2012 |
| WO | WO9315683 A1 | 8/1993 |
| WO | WO9521582 A1 | 8/1995 |

OTHER PUBLICATIONS

CAScination AG; "CAS-One IR: Stereotactic Navigation System for Interventional Radiology" https://www.cascination.ch/de/produkte/cas_one_ir; Jul. 18, 2019. pp. 1-6.

(Continued)

*Primary Examiner* — Todd J Scherbel
(74) *Attorney, Agent, or Firm* — Lempia Summerfield Katz LLC

(57) ABSTRACT

An improved guide for a medical needle is disclosed herein. An aligning element for aligning a needle guide, which is equipped for longitudinally guiding a medical needle, includes a connecting element for arranging the aligning element on the needle guide, and a light-guiding element for a predetermined diffusion of light. The light-guiding element only generates a predetermined light pattern relative to the diffusion of light in a pose predetermined by the geometry of the apparatus. Such an aligning element may be used in a treatment arrangement for longitudinally guiding a needle and in a method for aligning a needle guide.

10 Claims, 2 Drawing Sheets

(56) References Cited

U.S. PATENT DOCUMENTS

| | | |
|---|---|---|
| 2007/0055291 A1 | 3/2007 | Birkmeyer |
| 2008/0146963 A1 | 6/2008 | Crocker |
| 2012/0022508 A1 | 1/2012 | Gross |
| 2012/0209290 A1 | 8/2012 | Selover |
| 2017/0056062 A1 | 3/2017 | Buljubasic |

OTHER PUBLICATIONS

German Office Action for German Application No. 10 2018 215 599.2 dated May 2, 2019.
Dr. Alois Regensburger, Amilcar Alzaga, Horst-Günther Trautner "Improved Laser Needle Guidance"; Aug. 12, 2019. pp. 1-3.
European Search Report for European Application No. 19187258.9-1122 dated Feb. 3, 2020.

ALIGNING ELEMENT FOR GUIDING A NEEDLE, ALIGNING ARRANGEMENT, GUIDE ARRANGEMENT, TREATMENT ARRANGEMENT AND METHOD

The present patent document claims the benefit of German Patent Application No. 10 2018 215 599.2, filed Sep. 13, 2018, which is hereby incorporated by reference.

TECHNICAL FIELD

The disclosure relates to an aligning element for guiding a needle, which is equipped for longitudinally guiding a medical needle. The disclosure additionally includes an aligning arrangement with such an aligning element. Further aspects of the disclosure relate to a guiding arrangement and a treatment arrangement each for longitudinally guiding a medical needle. An additional part of the disclosure is a method for aligning a needle.

BACKGROUND

In many cases, it is necessary for medical treatments to insert a medical needle in a targeted manner, that is, along a precisely stipulated medical pathway into a subject (e.g., a patient). When treating areas inside the patient's body, (e.g., internal organs), precise guiding of the needle along the needle pathway is important to provide the correct pathway between tissue and bone and to guarantee the targeted treatment of the respective organ. In this context, it is possible to monitor an insertion procedure of the needle by fluoroscopy. The disadvantage of this is the high exposure to X-ray radiation.

U.S. Pat. No. 9,095,361 B2 discloses an alternative method for guiding a needle. Here, the needle is directed in the light from a light source into a desired needle-insertion angle, there being arranged on the needle a cap, through which a laser or other light may shine to guide the way to the target.

SUMMARY AND DESCRIPTION

The present disclosure addresses the problem of allowing an improved guidance for a medical needle.

The scope of the present disclosure is defined solely by the appended claims and is not affected to any degree by the statements within this summary. The present embodiments may obviate one or more of the drawbacks or limitations in the related art.

A first aspect of the disclosure relates to an aligning element for aligning a needle-guiding apparatus, which is equipped for longitudinally guiding a medical needle, including a connection element for arranging the aligning element on such a needle-guiding apparatus, and a light-guiding apparatus or element for a pre-determined diffusion of light or light distribution, wherein the light-guiding element only generates a predetermined light pattern in a pose that is predetermined by the geometry of the apparatus relative to the light distribution.

The pose is the combination of position and orientation in three-dimensional space. The predetermined pose may be stipulated with regard to five of its six degrees of freedom. Displacement along the longitudinal guide may be freely selectable as the only degree of freedom. In other words, the predetermined pose, in which the light-guiding element generates the predetermined light pattern may be fixed by the geometry of the light-guiding element with regard to two translatory degrees of freedom and three spatial angles.

For longitudinal guidance of the medical needle, the movement of the medical needle may be at least partially restricted by the needle guide at least along one spatial direction, (e.g., at least partially along two spatial directions). A movement of the needle in all spatial directions transverse to an elongation of the longitudinal guide may therefore be restricted or suppressed. Through the longitudinal guide, a movement of the needle is only possible parallel to the previously determined needle pathway if the needle guide is aligned according to the previously determined needle pathway.

The connecting element is embodied to create a mechanical connection between the aligning element and the needle guide. In particular, the connecting element is embodied to arrange the aligning element on the needle guide in a predetermined relative position or in a predetermined pose relative to the needle guide. The arrangement may be temporary or permanent. In other words, the connecting element may be embodied for alternate arrangement and removal of the aligning element on the needle guide or for fixed, (that is, not necessarily detachable), connection of the aligning element to the needle guide.

The predetermined diffusion of light advantageously may involve a diffusion of light or light distribution from a light source to display a needle pathway. In particular, the predetermined diffusion of light is a predetermined diffusion of laser light. For example, the predetermined diffusion of light is embodied, for example, such that two intersecting lines may be projected onto an insertion point, into which the medical needle is supposed to be inserted into a part of the body. Accordingly, the aligning element may be configured to be used in the intended manner with such a projection apparatus that includes the aforementioned light source. The light-guiding apparatus or element is embodied to generate the predetermined light pattern only if the predetermined diffusion of light or light distribution impinges on the light-guiding element from a spatial angle that is determined by the predetermined pose. The predetermined diffusion of light then impinges on the light-guiding element, in particular, at a spatial angle predetermined by the geometry of the light-guiding element, if the light-guiding element is located in the predetermined pose relative to the diffusion of light. The predetermined light pattern may ensue via the light-guiding element by appropriate reflection and/or absorption of at least some of the diffusion of light.

By the predetermined diffusion of light, a previously specified needle pathway along which the medical needle is to be guided is displayed or projected. In particular, two planes are spanned by the two lines that are projected onto the insertion point. Here, the needle pathway may correspond with an intersection line of the two planes spanned. Overall, the aligning element guarantees that an improved alignment of the needle guide is facilitated. The improved alignment of the needle guide results in a particularly precise guidance of the medical needle along the previously determined needle pathway. The use of such a needle guide makes it possible, in particular, to avoid or at least reduce the probability of treatment errors during insertion of the needle by a physician, for example, due to shaky hands.

According to a development, provision is made for the connecting element to be at least partially designed as a pin. The pin may be embodied to be similar to or at least partly correspond to the medical needle. This provides that the aligning element may be inserted into the needle guide or arranged on the needle guide by the connecting element in a similar way to the medical needle. In a position of the needle guide, in which the medical needle may be guided along the previously determined needle pathway, the part of the connecting element that is partly designed as a pin may be parallel to the needle pathway.

According to a development, provision is made for the light-guiding apparatus or element to have at least two identifiers in two different planes, (e.g., parallel planes), and for the identifiers only to be illuminated simultaneously in the predetermined pose of the aligning element by the predetermined diffusion of light or light distribution. In other words, the light-guiding element includes a plurality of identifiers, (that is, at least two identifiers), which are only illuminated simultaneously by the predetermined diffusion of light when the light-guiding element is located in the predetermined pose relative to the diffusion of light. This plurality of identifiers is also arranged, in particular, on the two different planes, (in particular, parallel planes). Advantageously, at least two identifiers are arranged in each of the two different planes. In a particularly advantageous embodiment, the at least two identifiers in a plane are not arranged in parallel with each other. In particular, the planes may be completely or partly perpendicular to the connecting element that is embodied as a pin. This allocation results in a particularly good detectability of the predetermined light pattern. In particular, the predetermined light pattern consists in the identifiers being simultaneously illuminated by the predetermined light pattern.

According to a development, the light-guiding element includes a first disc-shaped structure and a second disc-shaped structure, wherein the first and the second disc-shaped structures are each arranged in a different one of the planes, and wherein identifiers for the first plane are embodied as slits and identifiers for the second plane as markings that correspond therewith. In other words, the first and the second plane are arranged in the two different, (e.g., parallel), planes. Accordingly, the disc-shaped structures may likewise be parallel to each other. The predetermined light pattern may include the diffusion of light penetrating through the slits in the first plane and impinging through the slits onto the markings in the second plane. In particular, a marking corresponding with a slit with regard to a guide direction of the longitudinal guide, (that is, the direction along which the medical needle is guided through the longitudinal guide), is arranged below the respective slit. This results in a particularly simple and efficient geometry for the light-guiding element.

A second aspect of the disclosure relates to an aligning arrangement equipped for longitudinally guiding a medical needle, including an alignable needle guide, and the aligning element described in the aforementioned. The needle guide has also already been described in the aforementioned. For this reason, the previous statements made, and the features disclosed also apply to the needle guide, which is part of the aligning arrangement.

According to a development, provision is made for the needle guide to have the same component or device for accommodating the aligning element and for guiding the medical needle. In other words, the same component or device pertaining to the needle guide is embodied both for accommodating the aligning element and for guiding the medical needle. In other words, the aligning element, in particular, with the connecting element thereof, which is advantageously partly embodied as a pin, may be inserted into the component or device for the needle guide, which component or device is also embodied for longitudinal guidance of the medical needle. In this way, the needle guide may first be aligned with the aid of the aligning element and then (e.g., after removal of the aligning element) the needle may be guided by the same component or device. In particular, the component is a drilled hole.

According to a different embodiment, the needle guide and the aligning element are combined with each other in one piece. In this case, the needle guide may be fixedly connected to the aligning element. In this embodiment, in particular, no provision is made such that, for guiding the medical needle, the aligning element is detached or removed from the needle guide. As a result of the fact that the aligning element is displaced with regard to a needle pathway predetermined by the needle guide, the predetermined diffusion of light is displaced in a similar manner. The advantage of this embodiment is that the correct positioning of the needle guide may be monitored during the guiding of the needle.

According to a development, at least one of the two planes is aligned perpendicular to a guide direction of the needle guide. In one embodiment, both planes of the two different planes are aligned perpendicular to the guide direction. In other words, the needle guide is embodied to guide the medical needle transversally to at least one of the two different planes. Reference is made here to the planes on which the identifiers of the element are arranged. The arrangement described here has proved to be particularly advantageous.

According to a development, projections of the first and of the second disc-shaped structures overlap in the direction of the longitudinal guide onto one of the planes at least in some areas. In other words, the two planes overlap at least partly with regard to the guide direction of the needle guide. This embodiment allows an even more advantageous alignment of the needle guide.

A further aspect of the disclosure relates to a guiding arrangement for longitudinally guiding a medical needle, including an aligning arrangement of the aforementioned type, a fixing component to affix the guiding arrangement onto a patient-accommodating unit to receive a patient, and a holder to connect the needle guide and the fixing component together, wherein the holder includes at least one adjustment element for adjusting a relative position between the fixing component and the needle guide.

Accordingly, the guiding arrangement sets a relative position between the needle guide and the patient-accommodating unit. The fixing component may be, for example, a screw mechanism, a clamp mechanism, or any other mechanism for arranging the guiding arrangement on the patient-accommodating unit. The holder may be embodied, for example, as a telescopic arm with one or a plurality of pull-out and/or folding elements or as an adjustable track system. The needle guide may be arranged on the holder via a joint, such as a ball and socket joint. The adjustable element on the holder may be embodied as described in the aforementioned, as a folding mechanism and/or as a slide mechanism.

The patient-accommodating unit may be, for example, a chair or a couch. For example, the patient-accommodating unit may be an operating table, a bed, a stretcher, or any other piece of furniture on which the patient may be placed for treatment. Due to the fact that the patient is calmly residing on the patient-accommodating unit, the relative position between the patient and needle guide may be adjusted by the holder. In other words, the holder is embodied for adjusting the relative position between the needle guide and the patient when the guiding arrangement is arranged on the patient-accommodating unit and the patient is arranged on the patient-accommodating unit. The setting or adjusting of the relative position between the fixing component and the needle guide ensues, in particular, by the pose between the aligning element and the predetermined diffusion of light. Such a predetermined diffusion of light may be projected in the direction of the patient-accommodating unit, in particular, when the patient is arranged on the patient-accommodating unit.

The disclosure further includes a treatment arrangement for longitudinally guiding a medical needle, including a patient-accommodating unit to receive a patient, the aforementioned guiding arrangement, which is arranged on the patient-accommodating unit by the fixing component, and a light source for generating the predetermined diffusion of light according to a previously determined needle pathway along which the medical needle is to be guided relative to the patient-accommodating unit. The needle guide may be fixed by the holder in the predetermined pose. Additionally, it is only in the predetermined pose that by the diffusion of light a predetermined light pattern may be generated by the aligning element that is arranged on the needle guide. Further, the needle guide is embodied in the predetermined pose to guide the medical needle along the previously determined needle pathway. In particular, the light source has a predetermined relative position relative to the patient-accommodating unit and therefore also relative to the guiding arrangement. In this way, the predetermined diffusion of light may be projected in the intended manner, that is, according to the previously determined needle pathway, by the light source onto the patient-accommodating unit, and consequently onto the patient when the patient is arranged on the patient-accommodating unit.

The present disclosure additionally includes a method for aligning a needle guide, which is equipped for longitudinally guiding a medical needle. The method includes: generating a diffusion of light or light distribution by a previously determined needle pathway along which the medical needle is to be guided, and aligning the needle guide for the medical needle into a predetermined pose relative to the diffusion of light, wherein it is only in the predetermined pose that a predetermined light pattern is generated by the diffusion of light by an aligning element that is arranged on the needle guide.

In an optional additional process act, the needle pathway may be determined. For example, the needle pathway may be determined in the context of an X-ray examination. For example, in the context of the X-ray examination, a specific site or a specific organ (e.g., or the representation thereof in the simulation) of a patient or dummy to simulate a patient is sought. The needle pathway may then be calculated past bones to the site or to the organ.

The process act of aligning the needle guide may be carried out, for example, in an automated manner by at least one actuator on a holder or on an adjustment element of a guide arrangement described in the aforementioned. Alternatively, the act may be carried out by a robot or by a person, in particular, by a physician or their assistant. The insertion of the needle into a dummy used to simulate the patient by a needle guide that has been aligned in the aforementioned manner may be considered to be part of the disclosure.

For example, to align the needle guide, the aligning element is first arranged on the needle guide or attached onto the needle guide. After the needle guide has been aligned, the aligning element may be removed again in order to leave a longitudinal guide of the needle guide free to guide the needle through.

A development of the method makes provision for the diffusion of light or light distribution to be generated such that two spatial planes are spanned, and the needle pathway runs in parallel, in particular partly identical, to an intersection line of the two planes. In particular, the diffusion of light is generated by a light source pertaining to an aforementioned treatment arrangement. In the context of the development, provision may be made for the needle pathway to be visualized or represented by the intersection lines of the two planes that are spanned by the diffusion of light. Due to the predetermined diffusion of light or due to the planes that it spans, two intersecting lines may be projected onto an aforementioned patient-accommodating unit or onto the patient. The point of intersection of the two lines may then represent an insertion point.

Features and characteristics and developments that have been disclosed in the context of one aspect of the disclosure apply by analogy to all the claimed subject matter. For example, features that have been disclosed with reference to the aligning element, the needle guide and the aligning arrangement also apply by analogy to the guide arrangement, the treatment arrangement and the method. The method may be carried out with the aligning arrangement, the aligning element, the guiding arrangement, or the treatment arrangement described herein. Accordingly, the individual aspects of the disclosure each relate to one another.

BRIEF DESCRIPTION OF THE DRAWINGS

The disclosure is described in greater detail hereinafter with reference to the drawings.

DETAILED DESCRIPTION

Figure 1:
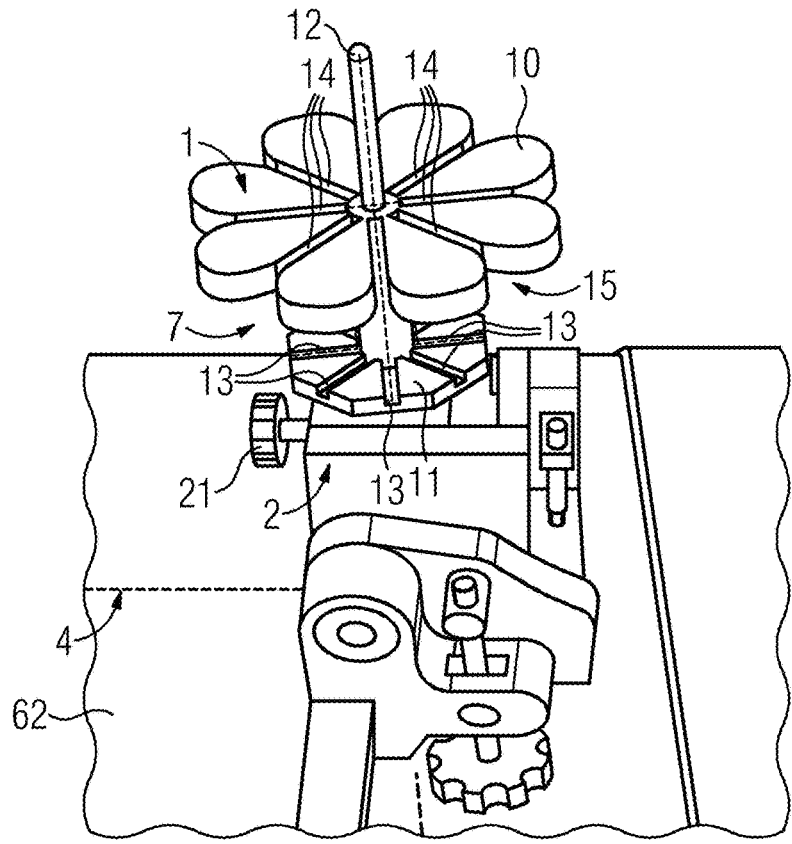
FIG. 1 depicts a schematic perspective view of an example of an aligning element in a needle guide.
Figure 3:
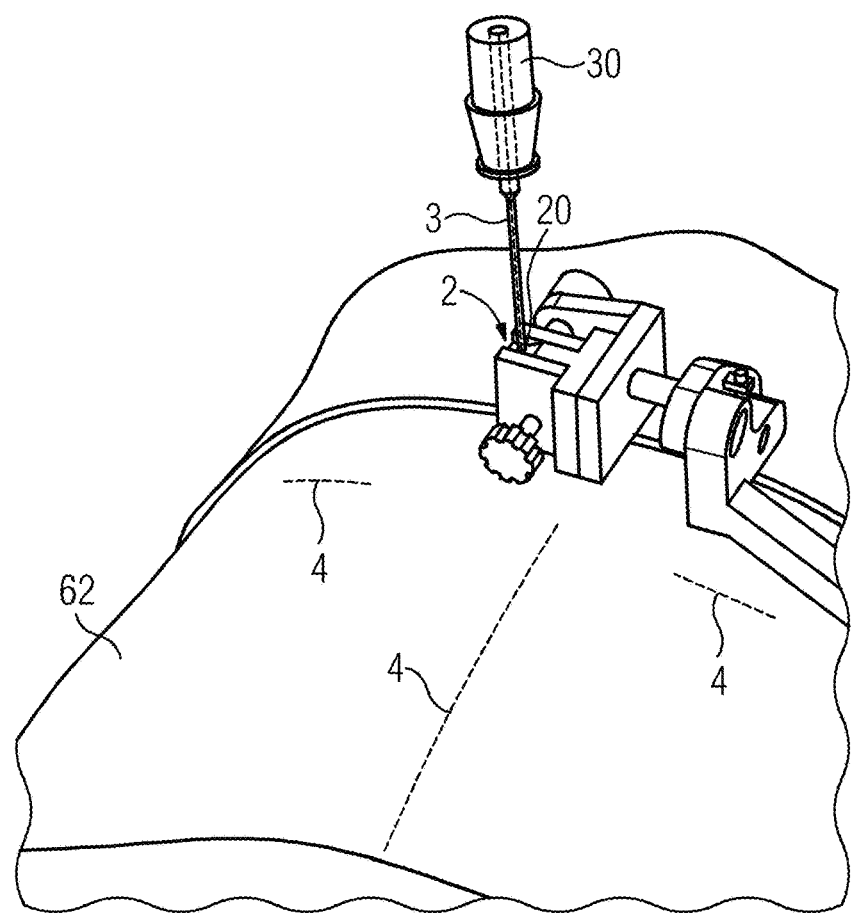
FIG. 3 depicts an example of the insertion of a medical needle into the needle guide.

FIG. 1 depicts an aligning element 1 and a needle guide 2. In summary, the aligning element 1 and the needle guide 2 form an aligning arrangement 7. The aligning element 1 is arranged according to FIG. 1 on a longitudinal guide 20 of the needle guide 2. The longitudinal guide 20 is indicated in FIG. 3 and in the present exemplary embodiment it is embodied as a drilled hole. This drilled hole is elongated, in particular, along a guide direction of the longitudinal guide 20. In this context, the term elongated refers to the depth of the drilled hole being greater than the diameter of the drilled hole. In particular, the depth is double the size or five times the size of the diameter of the drilled hole. In particular, the drilled hole runs through the entire needle guide 2. In other words, a medical needle 3 may be guided through the drilled hole. In this way, the longitudinal guide 20 pertaining to the medical needle is provided by the needle guide 2. In other words, due to the longitudinal guide 20, a movement of the needle 3 along two spatial directions is possible only to a limited extent or is not possible. In the present example, the longitudinal guide 20 therefore allows a movement of the needle 3 exclusively parallel with the guide direction of the longitudinal guide 20.

Figure 2:
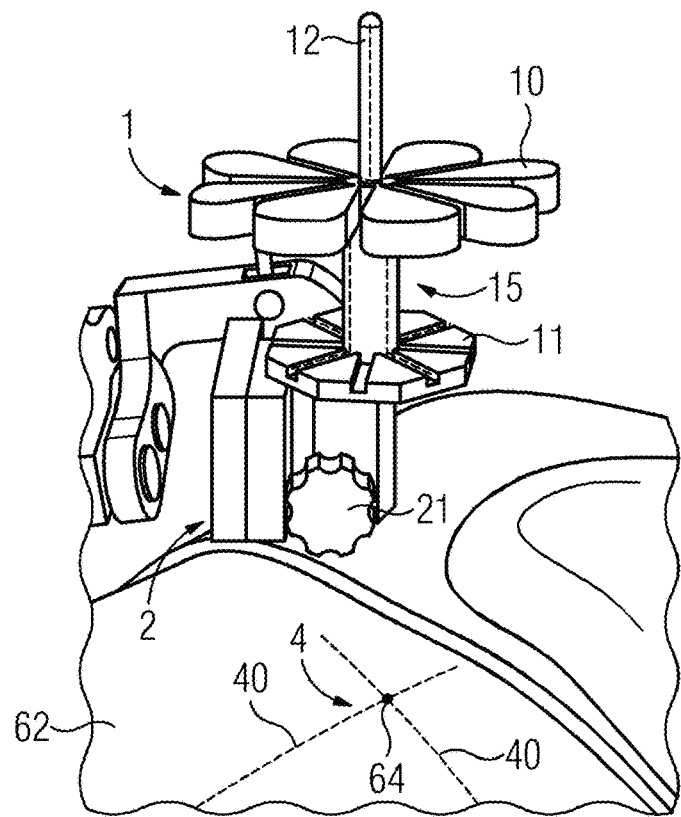
FIG. 2 depicts a further schematic perspective view of an example of the aligning element in the needle guide.

Reference is now made again to FIG. 1 and FIG. 2. The aligning element 1 is arranged on the needle guide 2 by a connecting element that is embodied as a pin. This pin of the connecting element is embodied in a similar way to a further pin 12. The pin of the connecting element is arranged on the opposite side of the aligning element 1 with respect to the pin 12. The pin of the connecting element runs, in particular, in a parallel extension to the pin 12. In FIG. 1 and FIG. 2, the connecting element and the pin thereof are not visible because the connecting element is located inside the needle guide 2. In particular, the connecting element or the pin thereof is arranged inside the longitudinal guide 20 or inside the drilled hole of the needle guide 2. In other words, the pin allows the aligning element 1 to be attached to the needle guide 2. During such an attachment, the pin is inserted into the drilled hole. The needle guide 2 optionally includes a locking mechanism 21 to lock the aligning element 1 onto the needle guide 2. In the present case, the locking mechanism 21 is embodied as a screw.

Figure 4:
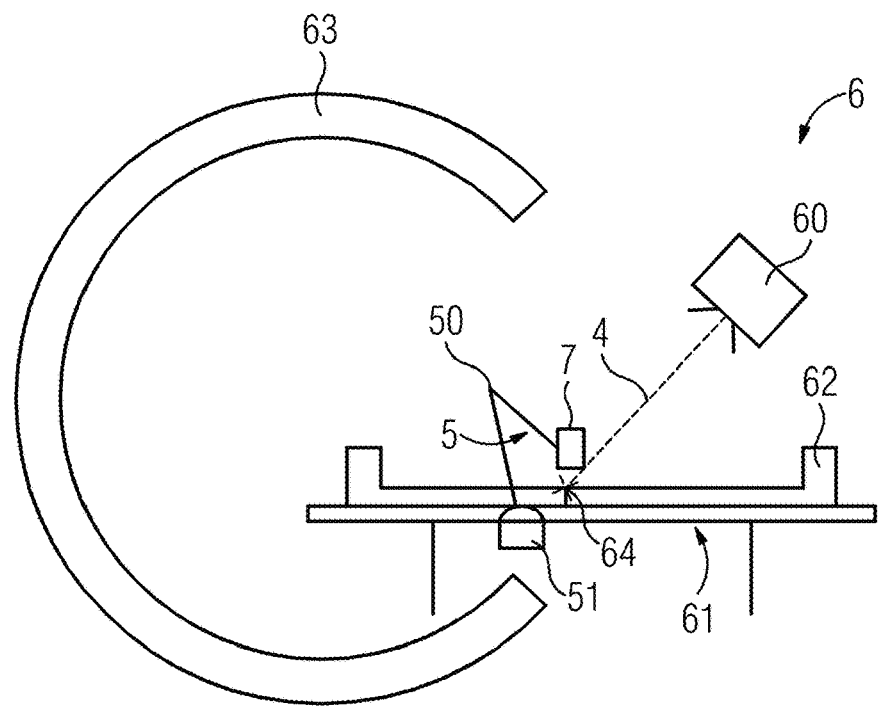
FIG. 4 depicts an example of a treatment arrangement including the needle guide and the aligning element.

FIG. 4 depicts a treatment arrangement 6, which includes a guiding arrangement 5, a light source 60 and a patient-accommodating unit 61. The guiding arrangement 5 includes in turn the aligning arrangement 7, a fixing component 51, and a holder 50. The light source 60 is embodied, for example, as a laser-light source or LED-light source. The patient-accommodating unit 61 may be an operating table, a bed, a treatment couch, or any suitable chair or couch. In the present case, the treatment arrangement 6 also includes an X-ray apparatus 63, in particular, a C-arm X-ray device. By the X-ray apparatus 63, a treatment in the context of which the medical needle 3 is inserted into a patient may be monitored. To this end, the X-ray apparatus 63 may perform a fluoroscopy.

In the present exemplary embodiment, the guiding arrangement 5 is arranged on the patient-accommodating unit 61 by the fixing component 51. This ensues, for example, by a screw mechanism, a clamp mechanism, or any other fixing mechanism of the fixing component 51. The holder 50 connects the aligning arrangement 7 or the needle guide 2 to the fixing component 51 and, in the event of it being affixed as intended onto the patient-accommodating unit 61, also connects it to the patient-accommodating unit 61.

The needle guide 2 is fixed by the holder 50 and the fixing component 51 relative to the patient-accommodating unit 61, wherein by the holder 50 an adjustment of the relative position between the needle guide 2 and the patient-accommodating unit 61 is facilitated. The holder 50 may include an adjustment element for adjusting the aforementioned relative position. In particular, such adjustment elements may be embodied as track mechanisms, folding mechanisms, or telescopic mechanisms. In particular the holder 50 includes a plurality of different types of adjustment elements. In this way, the guiding arrangement 5 or treatment arrangement 6 facilitates the fixing of the needle guide 2 into a predetermined position or pose relative to a treatment subject 62 arranged on the patient-accommodating unit 61. In a further embodiment, the holder 50 may include a motor (for example, an electric motor) or actuators for automatically adjusting the relative position. The treatment subject 62 may be, for example, a patient or a dummy for simulating a patient.

The treatment arrangement 6 allows a treatment of a patient with the medical needle 3 or a simulation of such a treatment using the dummy. An X-ray examination of the treatment subject 62 may be provided by the X-ray apparatus 63. In the context of this X-ray examination, a needle pathway for the medical needle 3 may be determined. For example, in the context of the X-ray examination, a specific site or a specific organ (or the representation thereof in the simulation) in the treatment subject 62 is sought. The needle pathway may then be calculated past bone to the site or to the organ. The diffusion of light or light distribution 4 is radiated by the light source 60 according to the previously determined needle pathway. By the diffusion of light 4, the needle pathway for the needle 3 is visualized. The diffusion of light 4 may also be seen in FIG. 2. By the diffusion of light 4, a projection 40 is projected onto the treatment subject 62. The projection 40 is shown in FIG. 2 in the form of two perpendicular lines. The point of intersection of the perpendicular lines in the projection 40 corresponds with a predetermined insertion point 64 for the needle 3. Accordingly, by the diffusion of light 4, two spatial planes are spanned. Here, the planes may connect the projection 40 to the light source 60. The projection 40 may therefore be seen as a projection of the two planes spanned in parallel with the diffusion of light 4 onto the surface of the treatment subject 62.

There next ensues an alignment of the needle guide 2 by the diffusion of light 4 with the aid of the aligning element 1. In FIG. 1 and FIG. 2 in turn, a light-guiding apparatus or element 15 of the aligning element 1 may be seen. The light-guiding element 15 is embodied such that the light-guiding element is only in a pose that is predetermined by its geometry relative to the diffusion of light 4 that a predetermined light pattern is generated. To this end, the light-guiding element 15 includes two disc-shaped structures 10 and 11. The two disc-shaped structures 10, 11 are arranged in different planes. In particular, the two disc-shaped structures 10, 11 or the planes in which the disc-shaped structures 10, 11 are arranged each run perpendicular to the pin 12 or to the pin of the connecting element. Accordingly, the disc-shaped structures 10, 11 run parallel to the guide direction of the longitudinal guide 20 when the aligning element 1 is arranged on the needle guide 2 as intended.

In the present exemplary embodiment, the disc-shaped structure 10 includes slits 12. The slits 12 serve as identifiers for the corresponding plane. The disc-shaped structure 11 includes markings 13. The respective markings 13 each correspond with one of the slits 12. In particular, each slit 12 in the guide direction is arranged above the corresponding marking 13. In the present case, the aligning element 1 includes two light-guiding elements 15. In the present exemplary embodiment, each of the light-guiding elements 15 has four slits 12 and four markings 13. The present aligning element 1 therefore includes a total of eight slits 12 and eight markings 13 (see reference signs). The light-guiding elements 15 are rotated by 45° relative to each other.

If the needle guide 2 is now in a predetermined pose relative to the diffusion of light 4, then the diffusion of light 4 penetrates through the slits 12 onto the markings 13. Within the treatment arrangement 6 is located the light source 60 and therefore also the diffusion of light 4 in a defined position relative to the patient-accommodating unit 61. It is therefore only in the predetermined pose relative to the diffusion of light 4 that all the markings 13 of a light-guiding element 15 are illuminated through the corresponding slits 12 by the diffusion of light 4. This corresponds to a predetermined light pattern, which is generated by the corresponding light-guiding element 15. The light pattern is represented in FIG. 1 and FIG. 2 by dotted lines on the aligning element 1. In this way, the needle guide 2 may be aligned onto the previously determined needle pathway with the aid of the aligning element 1 and with the aid of the diffusion of light 4. For example, the needle guide 2 is aligned by adjusting the holder 50 to correspond with the diffusion of light 4. This alignment may be performed, for example, by the motor or the actuators on the holder 50, by a separate robot or by a person, in particular, by a physician or their assistant.

As shown in FIG. 3, the aligning element 1 may be removed and the medical needle 3 may be guided through the longitudinal guide 20. The insertion of the needle 3 into the treatment subject 62 may be monitored by the X-ray apparatus 63. The insertion of the needle 3 into a dummy used to simulate the patient, by a needle guide 2 that has been aligned in the aforementioned manner, may be considered to be part of the disclosure.

In the present embodiment, the aligning element 1 is an attachable aligning element 1. Due to the type and shape thereof, the aligning element 1 may also be described as an "attachable flower-head". The alignment of the aligning element 1, in particular, of the connecting element and/or of the pin 12, corresponds to the alignment of the longitudinal guide 20 or of the needle pathway that is predetermined by the longitudinal guide 20. Corresponding straight lines that are defined by the longitudinal guide 20 and by the aligning element 1 are accordingly parallel and, in particular, identical. In different embodiments, the aligning element 1 may be fixedly connected to the needle guide 2. In this case, the aligning element 1 may be part of the needle guide 2 and/or be combined in one piece with the needle guide. In this case, the aligning element, in particular, is not in the needle pathway predetermined by the longitudinal guide 20. In this case, the aligning element 1 may be moved around a fixed position relative to the longitudinal guide 20 or to the needle pathway predetermined by the guide 20. For this reason, it may be necessary to move the diffusion of light 4 around the same fixed relative position. As a result, the correct needle pathway corresponding with the previously determined needle pathway may also be guaranteed in this case.

The exemplary embodiment shows how accuracy may be improved when aligning a needle guide. Furthermore, improved accuracy in the insertion of a medical needle may be facilitated. By the optimally aligned needle guide, first incorrect positioning of the needle and second, any tremor on the part of the physician may be counteracted.

Although the disclosure was illustrated and described in more detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. An aligning element for aligning a needle guide, which is equipped for longitudinally guiding a medical needle, the aligning element comprising:
   a connecting element for arranging the aligning element on the needle guide; and
   a light-guiding element for predetermined diffusion of light,
   wherein the light-guiding element only generates a predetermined light pattern in a pose relative to the diffusion of light, wherein the pose is predetermined by a geometry of the light-guiding element,
   wherein the light-guiding element comprises at least two identifiers on two different parallel planes, and
   wherein the at least two identifiers are only illuminated simultaneously by the predetermined diffusion of light in the predetermined pose of the aligning element.

2. The aligning element of claim 1, wherein the connecting element is at least partly embodied as a pin.

3. The aligning element of claim 1, wherein the light-guiding element comprises a first disc-shaped structure and a second disc-shaped structure,
   wherein the first and the second disc-shaped structures are each arranged in a different plane of the two different parallel planes, and
   wherein identifiers of the at least two identifiers in a first plane of the two different parallel planes are embodied as slits and identifiers of the at least two identifiers in a second plane of the two different parallel planes are markings corresponding with the slits.

4. An aligning arrangement configured to longitudinally guide a medical needle, the aligning arrangement comprising:
   an adjustable needle guide; and
   an aligning element comprising:
      a connecting element for arranging the aligning element on the adjustable needle guide; and
      a light-guiding element for predetermined diffusion of light,
      wherein the light-guiding element only generates a predetermined light pattern in a pose relative to the diffusion of light, wherein the pose is predetermined by a geometry of the light-guiding element,
      wherein the light-guiding element comprises at least two identifiers
      wherein the at least two identifiers are only illuminated simultaneously by the predetermined diffusion of light in the predetermined pose of the aligning element.

5. The aligning arrangement of claim 4, wherein the adjustable needle guide comprises a same component for accommodating the aligning element and for guiding the medical needle.

6. The aligning arrangement of claim 4, wherein the adjustable needle guide and the aligning element are combined with each other in one piece.

7. The aligning arrangement of claim 4, wherein at least one plane of the two different parallel planes is aligned perpendicular to a guide direction of the adjustable needle guide.

8. The aligning arrangement of claim 4, wherein the light-guiding element comprises a first disc-shaped structure and a second disc-shaped structure,
   wherein the first and the second disc-shaped structures are each arranged in a different plane of the two different parallel planes, and
   wherein identifiers of the at least two identifiers in a first plane of the two different parallel planes are embodied as slits and identifiers of the at least two identifiers in a second plane of the two different parallel planes are markings corresponding with the slits.

9. A guiding arrangement configured to longitudinally guide a medical needle, the guiding arrangement comprising:

an aligning arrangement having an adjustable needle guide and an aligning element, the aligning element comprising:
  a connecting element for arranging the aligning element on the adjustable needle guide; and
  a light-guiding element for predetermined diffusion of light,
  wherein the light-guiding element only generates a predetermined light pattern in a pose relative to the diffusion of light, wherein the pose is predetermined by a geometry of the light-guiding element,
  wherein the light-guiding element comprises at least two identifiers on two different parallel planes, and
  wherein the at least two identifiers are only illuminated simultaneously by the predetermined diffusion of light in the predetermined pose of the aligning element;
a fixing component configured to affix the guiding arrangement onto a patient-accommodating unit to receive a patient; and
a holder configured to combine the adjustable needle guide with the fixing component, wherein the holder comprises at least one adjustment element for adjusting a relative position between the fixing component and the adjustable needle guide.

10. A treatment arrangement configured to longitudinally guide a medical needle, the treatment arrangement comprising:
  a patient-accommodating unit configured to receive a patient;
  a guiding arrangement having:
    an aligning arrangement having an adjustable needle guide and an aligning element, the aligning element comprising:
      a connecting element for arranging the aligning element on the adjustable needle guide; and
      a light-guiding element for predetermined diffusion of light,
      wherein the light-guiding element only generates a predetermined light pattern in a pose relative to the diffusion of light, wherein the pose is predetermined by a geometry of the light-guiding element,
      wherein the light-guiding element comprises at least two identifiers on two different parallel planes, and
      wherein the at least two identifiers are only illuminated simultaneously by the predetermined diffusion of light in the predetermined pose of the aligning element;
    a fixing component that affixes the guiding arrangement onto the patient-accommodating unit to receive the patient; and
    a holder configured to combine the adjustable needle guide with the fixing component, wherein the holder comprises at least one adjustment element for adjusting a relative position between the fixing component and the adjustable needle guide; and
  a light source configured to generate the predetermined diffusion of light according to a previously determined needle pathway along which the medical needle is to be guided relative to the patient-accommodating unit,
  wherein the adjustable needle guide is configured to be fixed in the predetermined pose by the holder,
  wherein, only in the predetermined pose, a predetermined light pattern is configured to be generated by the diffusion of light by the aligning element arranged on the adjustable needle guide, and
  wherein the adjustable needle guide is configured to guide the medical needle in the predetermined pose along the previously determined needle pathway.

* * * * *